United States Patent [19]

Mares

[11] B 3,988,319

[45] Oct. 26, 1976

[54] PROCESS FOR PRODUCING CAPROLACTAM FROM 6-AMINOCAPROIC ACID

[75] Inventor: Frantisek Mares, Whippany, N.J.

[73] Assignee: Allied Chemical Corporation, New York, N.Y.

[22] Filed: Sept. 16, 1974

[21] Appl. No.: 506,148

[44] Published under the second Trial Voluntary Protest Program on February 3, 1976 as document No. B 506,148.

[52] U.S. Cl. .......................................... 260/239.3 A
[51] Int. Cl.$^2$ ...................................... C07D 201/08
[58] Field of Search ............................. 260/239.3 A

[56] References Cited

FOREIGN PATENTS OR APPLICATIONS 30-6112   8/1955   Japan ........................... 260/239.3 A

*Primary Examiner*—Henry R. Jiles
*Assistant Examiner*—Robert T. Bond
*Attorney, Agent, or Firm*—Robert A. Harman; Arthur J. Plantamura

[57] ABSTRACT

Caprolactam is obtained in high yield and in short reaction time by completely dissolving 6-aminocaproic acid in methanol or ethanol and heating the solution at 170°–200° C.

3 Claims, No Drawings

PROCESS FOR PRODUCING CAPROLACTAM FROM 6-AMINOCAPROIC ACID

BACKGROUND OF THE INVENTION

This invention relates to production of the commercially valuable compound caprolactam.

It is known that caprolactam is produced upon heating 6-aminocaproic acid or ethyl ester thereof. A low molecular weight molecule (water, ethyl alcohol) is split out and caprolactam is formed, along with greater or lesser amounts of polymeric materials.

Japanese patent publication No. 6112/1955 (Chemical Abstracts, Volume 51, 1957 at column 17984-h) is of particular interest in connection with the present invention. In accordance with this prior art publication, a dilute solution of 6-aminocaproic acid, in methanol or ethanol, is converted by heating at 220°–230°C. for 2–3 hours to caprolactam in 88% of theory yield. A small amount of ester (about 1%) is also recovered. The balance is unaccounted for.

SUMMARY OF THE INVENTION

I have now found that by operating along the lines of the above Japanese patent publication, but at temperatures low enough to exclude any formation of esters, caprolactum is produced in shorter time and in much better yields than appears from the cited Japanese patent publication. In my process, it is important that the 6-aminocaproic acid be completely dissolved before the solid reacts to any substantial extent in its solid state. To promote solution and the desired reaction, a rather narrow temperature range of 170°–200°C. is employed in my invention. Otherwise, the conditions are as in the above cited Japanese patent publication.

Although it is not intended to limit this invention by the correctness of any theory, it is believed the superiority of the results obtained by this invention using temperatures not above 200°C., as against use of higher temperatures in alcohol solution, can be explained as follows. Methanol and ethanol at elevated temperatures, such as 170°C., are reasonably good solvents for 6-aminocaproic acid. However, they are not sufficiently polar to dissolve the acid in the form of the open chain zwitterion $(NH_3^+)(CH_2)_5CO_2^-$ which is the dissolved form in highly polar solvent such as water. Accordingly, 6-aminocaproic acid in relatively dilute solution as occurs in these alcohol solvents forms dissolved cyclic intra molecular zwitterion rather than open chain molecules. At the temperature range 170°–200°C., the cyclic intra molecular zwitterion loses water and forms caprolactam in the present process. Open chain molecules, on the other hand, form open chain dimeric (and higher) polyamides in addition to the cyclic product, caprolactam.

However, if the above operations are conducted at 220°C. or higher temperatures, the tendency for formation of the ester alkyl 6-aminocaproate, is increased. The ester formed then cyclizes to caprolactam substantially slower than 6-aminocaproic acid. Consequently the free, unprotonated —$NH_2$ groups provided by the ester remain present in the reaction mixture. These amino groups are basic enough to promote equilibrium between caprolactam, oligomers and alkyl 6-aminocaproate. As a result of the approach toward this equilibrium a lower yield of caprolactam, and appreciable oligomer formation is obtained. This formation of oligomers is believed to account for the losses of material in the Japanese patent publication example, amounting to about 10%.

My relatively mild, dilute solution conditions which promote the cyclic intramolecular zwitterion structure and exclude formation of ester may account for my higher yield and faster conversion to lactam than obtained under conditions where the ester is formed.

Preferred embodiments of my invention are illustrated by the specific example of practice thereof which follows.

EXAMPLE

An autoclave with provision for good stirring was purged with nitrogen to remove air whereby to avoid discoloration of the lactam product by action of air at elevated temperature on the amino group of the starting material. The autoclave was charged with 30 ml. (23.62 grams) of ethanol and with 4.5 grams of 6-aminocaproic acid; and with 2 grams of diethylene glycol dimethyl ether to serve as internal standard in the analysis of the product by gas chromotography. With good stirring to insure complete dissolution of the amino acid before reaction sets in, the autoclave was heated to about 200°C. A sample taken about ½ hour after the temperature reached 200°C showed epsilon caprolactam content amounting to about 98 mol percent based on the amino acid starting material. Subsequent samples taken up to two hours after the start of heating showed caprolactam yields remaining at 98% of theory.

Similar results can be expected when methanol is the solvent. To avoid reaction of the aminocaproic acid prior to its complete dissolution, the substance should be added slowly enough so that no solid acid collects in the solvent, but instead the acid is practically immediately dispersed and completely dissolved in the hot solvent, or is well dispersed during heat-up.

The process can be operated continuously in a tubular reactor with preliminary mixing to form the solution desired, or in a stirred vessel with continuous or intermittent addition of starting material and withdrawal of product.

Since water is formed in the process as a coproduct with lactam, it is evident that the alcohol used need not be anhydrous. However, if the water content is too high, over 40 volume percent, there will be losses due to formation of open chain polyamides; so that when the alcohol solvent is recycled, water must periodically be separated.

I claim:

1. In a process of converting 6-aminocaproic acid, dissolved in methanol or ethanol, to epsilon caprolactam the improvement comprising dissolving said acid in solvent containing at least 60 percent by volume of ethanol, methanol or a mixture thereof, under conditions such that no substantial reaction occurs prior to complete dissolution; and thereafter maintaining the resulting solution at temperature in the range of 170°–200°C.

2. The process of claim 1 wherein the solvent is ethanol and the reaction temperature is 200°C.

3. The process of claim 1 wherein the solvent is methanol.

* * * * *